(12) United States Patent
Maga et al.

(10) Patent No.: US 9,965,840 B2
(45) Date of Patent: May 8, 2018

(54) DEVICE AND METHOD FOR DETERMINING WEIGHT, IN PARTICULAR THE WEIGHT OF A CONTAINER FILLED WITH PRODUCT

(71) Applicant: Robert Bosch GmbH, Stuttgart (DE)

(72) Inventors: Iulian Maga, Ludwigsburg (DE); Martin Vogt, Schorndorf (DE); Jens Schlipf, Freiberg A. N. (DE)

(73) Assignee: Robert Bosch GmbH, Stuttgart (DE)

( * ) Notice: Subject to any disclaimer, the term of this patent is extended or adjusted under 35 U.S.C. 154(b) by 142 days.

(21) Appl. No.: 14/900,173

(22) PCT Filed: May 26, 2014

(86) PCT No.: PCT/EP2014/060801
§ 371 (c)(1),
(2) Date: Dec. 21, 2015

(87) PCT Pub. No.: WO2014/202340
PCT Pub. Date: Dec. 24, 2014

(65) Prior Publication Data
US 2016/0140413 A1    May 19, 2016

(30) Foreign Application Priority Data
Jun. 19, 2013    (DE) .......................... 10 2013 211 526

(51) Int. Cl.
*G06T 7/00*      (2017.01)
*G01N 23/04*   (2018.01)
(Continued)

(52) U.S. Cl.
CPC .............. *G06T 7/0004* (2013.01); *B65B 3/26* (2013.01); *G01G 9/005* (2013.01); *G01N 23/04* (2013.01);
(Continued)

(58) Field of Classification Search
None
See application file for complete search history.

(56) References Cited

U.S. PATENT DOCUMENTS 5,561,696 A * 10/1996 Adams ................. G01N 23/043
378/58
7,596,275 B1 * 9/2009 Richardson .......... G01V 5/0016
250/358.1
(Continued)

FOREIGN PATENT DOCUMENTS

JP      10239251       9/1998
JP     2006308467    11/2006
(Continued)

OTHER PUBLICATIONS

International Search Report for Application No. PCT/EP2014/060801 dated Jul. 18, 2014 (English Translation, 3 pages).

*Primary Examiner* — Kim Vu
*Assistant Examiner* — Nathan Bloom
(74) *Attorney, Agent, or Firm* — Michael Best & Friedrich LLP

(57) ABSTRACT

The invention relates to a device and a method for determining the weight of product (2), in particular a pharmaceutical product, which is located in a container (3). The device comprises at least one x-ray source (28), which produces a radiation path (18), for passing radiation through the container (3), and a sensor (14), which detects the radiation of the container (3) through which radiation is passed in the form of an image (12), wherein an evaluating apparatus (14), is provided, which divides the image (12) of the container (3) through which radiation is passed into at least one evaluation region (21) in which there is no product (2).

13 Claims, 5 Drawing Sheets

(51) Int. Cl.
  *G06T 7/62* (2017.01)
  *G06T 7/11* (2017.01)
  *G06T 7/13* (2017.01)
  *B65B 3/26* (2006.01)
  *G01N 23/10* (2018.01)
  *G01N 33/15* (2006.01)
  *G01G 9/00* (2006.01)
  *B65B 3/00* (2006.01)
  *A61J 3/07* (2006.01)
  *G01G 17/00* (2006.01)

(52) U.S. Cl.
  CPC ............ *G01N 23/10* (2013.01); *G01N 33/15* (2013.01); *G06T 7/11* (2017.01); *G06T 7/13* (2017.01); *G06T 7/62* (2017.01); *A61J 3/074* (2013.01); *B65B 3/003* (2013.01); *G01G 17/00* (2013.01); *G06T 2207/10116* (2013.01); *G06T 2207/30108* (2013.01)

(56) References Cited

U.S. PATENT DOCUMENTS

| | | | |
|---|---|---|---|
| 2008/0049899 A1* | 2/2008 | Rothschild | G01N 23/20 378/86 |
| 2008/0219803 A1* | 9/2008 | Runft | A61J 3/074 414/21 |
| 2010/0202694 A1* | 8/2010 | Kabumoto | G01N 21/3581 382/190 |
| 2011/0277871 A1* | 11/2011 | Trebbi | A61J 3/074 141/1 |

FOREIGN PATENT DOCUMENTS

| | | | |
|---|---|---|---|
| JP | 2006308467 A | * | 11/2006 |
| WO | 2006106012 | | 10/2006 |
| WO | 2012013368 | | 2/2012 |

* cited by examiner

DEVICE AND METHOD FOR DETERMINING WEIGHT, IN PARTICULAR THE WEIGHT OF A CONTAINER FILLED WITH PRODUCT

BACKGROUND OF THE INVENTION

The invention proceeds from a device and a method for determining the weight of pharmaceutical products by means of an x-ray source. A generic device and method are already known from WO 2012/013368 A1. An x-ray source produces a radiation cone which irradiates at least one pharmaceutical product. A sensor element detects the radiation of the irradiated pharmaceutical product and feeds it to an evaluation device. A reference object is arranged in the radiation path of the radiation cone, the radiation of the x-rayed reference object being detected by means of sensor elements and fed to the evaluation unit, the pharmaceutical product and the reference object being positioned with reference to the radiation cone in a non-congruent arrangement with one another in the radiation cone.

SUMMARY OF THE INVENTION

It is an object of the present invention further to improve the accuracy of the determination of weight.

The device according to the invention and the method according to the invention have, by contrast, the advantage that the measuring accuracy can be markedly increased with reference to the net weight. It is therefore possible to have a 100% inline net weight determination during normal operation with high accuracy without the use of a gravimetric load cell. This is because the device according to the invention and the method according to the invention make use of specific information from, in particular, digital images of the containers filled with pharmaceutical products in order to determine the net weight with a higher accuracy than would be possible with a conventional gross weight determination. This is possible, in particular, because the weight of an empty container is determined on the basis of the part of a container which can be freely x-rayed, in particular the part thereof in which no product is located. This determined tare weight value is subsequently subtracted from the gross weight. The result is the net weight of the product located in the container. The evaluation can take place with the aid of only a single x-ray image. The net weight of the product, which is of greatest interest, is hence determined in targeted fashion, and no longer only the gross weight of container and product, as in the prior art. This is particularly advantageous especially in the case of small filling quantities, since in said instances the weight of the container greatly influences the accuracy of the determination of weight. Thus, given small filling quantities, manufacturing fluctuations in the tare weight of empty containers can be greater than maximum permissible fluctuations in filling quantities. This can result in containers with the correct filling quantity of the product being rejected as incorrectly filled, because the tare weight of the container has exhausted the weight tolerance. Conversely, this can also have the effect that a container filled with too much or too little filled product is wrongly recognized as being in order, because the tolerated container weight fluctuation has the opposite effect and compensates the erroneous dosing. The net weight determination described counteracts said unacceptable cases particularly advantageously.

In an expedient development, it is provided that the evaluation device determines the tare weight of the container in that the evaluation device forms the ratio between a measure of an area of the evaluation region and a measure of an area of a contour of the entire irradiated container. It is particularly preferred to make use as measure of an area of the evaluation region and/or of the contour of such pixels of the sensor that lie within the evaluation region and/or within the contour. It is particularly easy to use the information of the flat sensor to extrapolate the tare weight to the entire container without the need for additional sensors or measurements. The structure of the device is thereby simplified.

In an expedient development, it is provided that the evaluation device evaluates gray scale values and/or pixels of the sensor lying within the evaluation region and/or the contour in order to determine the weight. The accuracy of the determination of weight can be further increased by a targeted evaluation of the regions of interest. It is easy for variables corrupting the net weight determination to be removed by calculation.

In an expedient development, it is provided that the device is trained to the containers being used, in particular empty containers. For this purpose, it is preferred to construct a reference line of the container material, in which case the reference to the gravimetric weight could be done with the aid of very accurate scales (tare adjustment).

In an expedient development, it is provided that the device is trained to containers with filled product. In this case, the reference line of a container with product is constructed, it being possible for the reference to the gravimetric weight to be made with the aid of very accurate scales (gross adjustment).

In an expedient development, it is provided that the device comprises means for imaging the container to be tested. A specific evaluation region is prescribed in targeted fashion. Said region is preferably in such a container area as is not filled with a product. Subsequently, said region of the part of the container which can be freely x-rayed is evaluated. This is done by using said part of the container which can be freely x-rayed, and by using the determined reference line in the course of the tare adjustment and extrapolation to the empty weight of a container (tare weight).

In an expedient development, it is provided that the entire container, including the product, can now be evaluated with recourse to the already determined image. The gross weight is determined on the basis of this information and the reference line as determined in the course of the gross adjustment.

In an expedient development, it is provided that the net weight of the container to be tested is determined by forming the difference between the gross weight and the tare weight, as determined in the prior method steps.

In an expedient development, it is provided that at least one reference object is provided which is arranged in the radiation path of the x-ray source and which has different thicknesses, in which case, in order to determine the net weight, the evaluation unit respectively assigns the gray scale values of the differential image a thickness of the reference object which corresponds to the gray scale value of the reference object. It is precisely owing to the use of a reference object having different thicknesses which is likewise irradiated together with the container during operation that it is possible to convert the gray scale values reliably into a net weight. This can be performed in a particularly simple and accurate way with the aid of the corresponding thicknesses, conversion into a volume and assignment to a net weight by means of the reference line.

In an expedient development, it is provided that at least a second reference object is provided which is arranged in the radiation path of the x-ray source and has different thicknesses. It would be possible in this case for one of the reference objects to be adapted to the material of an empty container, and for the other to be adapted to the container filling. The more that the empty container and product differ from one another with reference to their absorption properties, the greater the increases in accuracy that can be attained thereby. During the tare adjustment, the reference object tuned to the empty container would be used to construct the reference line. During the gross adjustment, the further reference object tuned to the container filling would be used to construct the reference line. During the subsequent actual measurement, the empty container extrapolation is carried out again with the aid of the reference object tuned to the empty container, and the gross measurement is carried out with the aid of the further reference object tuned to the container filling. Consequently, conversion into virtual volume and thus into the weight is carried out in a differentiated manner, depending on the material being considered, and leads to a once more improved accuracy.

In an expedient development, an accommodating means, in particular a capsule holder, is provided for accommodating at least one container, the container being fed via a conveying means to a processing station and/or the x-ray source in order to produce the image. Said arrangement is suitable, in particular, for containers which are fed to different workstations at high speed. It is possible thereby to achieve high throughput rates.

BRIEF DESCRIPTION OF THE DRAWINGS

An exemplary embodiment of the device according to the invention and of the method according to the invention are illustrated in the drawing and described in more detail below.

In the drawing.

DETAILED DESCRIPTION

Figure 1:
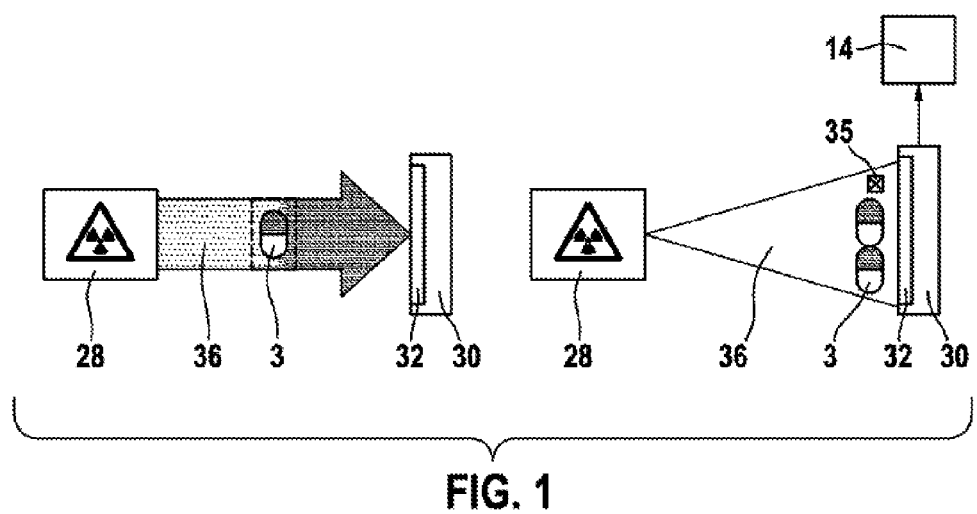
FIG. 1 shows the fundamental principle of imaging, which is based on x-radiation.

A plurality of containers 3 are located in a radiation path 36 of an x-ray source 28 which irradiates the containers 3. Located downstream is a sensor 30 with a sensor surface 32 which faces the x-ray source 28. The sensor 30 serves to produce an x-ray image or image 12 of the irradiated container. The sensor surface 32 preferably comprises a multiplicity of radiation-sensitive sensor elements such as, for example, CCD sensors or CMOS sensors which, depending on the incident radiation, respectively emit an output signal which is referred to below as gray scale value. By way of example, to this end a scintillation layer which converts the x-ray energy into visible light is applied over the pixels of the CMOS sensor. As a function of the light quantity, the pixel of the sensor generates a charge (analog) which is preferably converted into a digital signal ("gray scale value") which is used for determining weight. The image 12 is produced via the output signals of the sensor elements arranged in two dimensions. It is also possible in principle to use other radiation detecting means as sensors.

In the right-hand exemplary embodiment of FIG. 1, there is also located a reference element 35 in the radiation path 36 of the x-ray source 28. The reference element 35 is arranged non-congruently next to the containers 3 and is likewise irradiated. The image 12 thereby produced is likewise recorded by the sensor 30.

Figure 2:
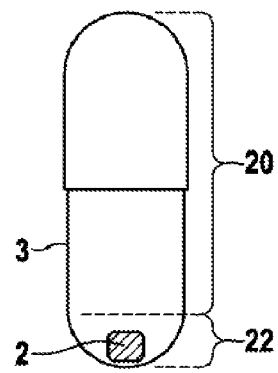
FIG. 2 shows a partially filled container.

The container 3 in accordance with FIG. 2 is, for example, a capsule in which there is partially located a product 2 such as, for example, a pharmaceutical product. The container 3 thus has a region 20 which can be freely x-rayed and in which no product 2 is located, and a region 22 which cannot be freely x-rayed and in which the product 2 is located.

Figure 3:
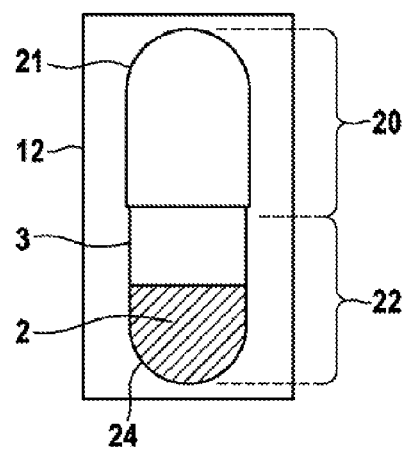
FIG. 3 shows an image of a filled container with established evaluation regions.

In FIG. 3, the container 3, in turn, has a region 22 which cannot be freely x-rayed, and a region 20 which can be freely x-rayed. An evaluation region 21 is now established for the region 20 which can be freely x-rayed, this being done in such a way that there is certainly no product 2 located within the evaluation region 21. Moreover, a contour 24 of the container 3 which corresponds to the outer contour is established via a threshold value evaluation of the gray tones.

Figure 4:
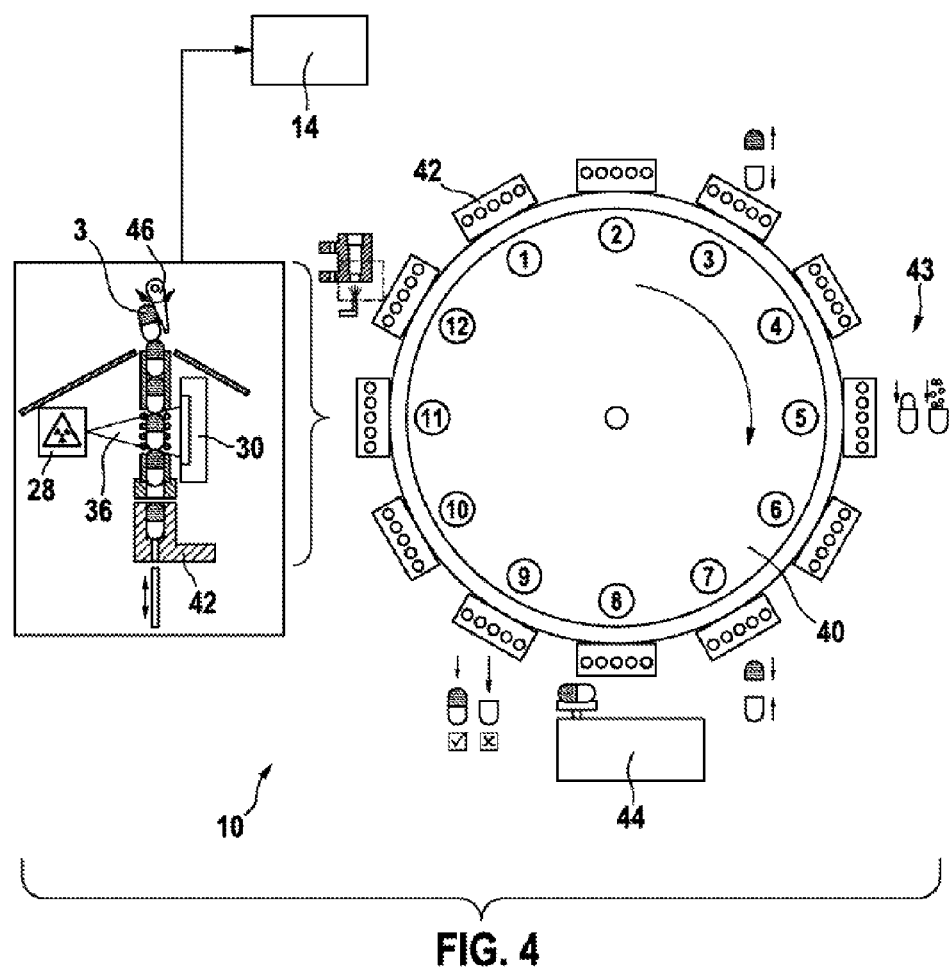
FIG. 4 shows a device according to the invention.
Figure 5:
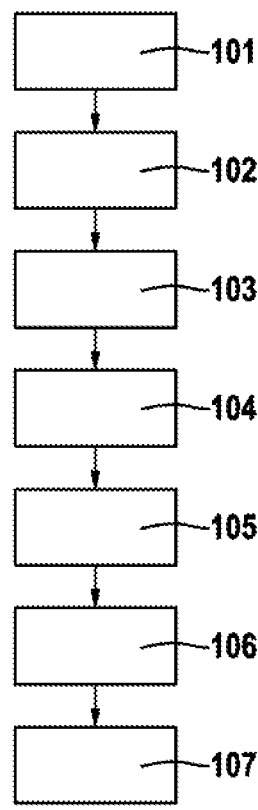
FIG. 5 shows a flowchart of the method according to the invention.

FIG. 4 shows the device 10 which is suitable for carrying out the method described. This is described in an exemplary manner using the concrete example of a capsule filling machine for which the invention is particularly suited, but is not restricted thereto.

A machine for filling and closing the container 3 consisting of a capsule base and a plug-on cap has a twelve-part conveyor wheel 40 which is turned in stepwise fashion about a vertical axis and at whose stations 1 to 12 the individual handling devices are arranged on the revolving section. Other divisions of the conveyor wheel 40 would also be conceivable, for example into 15 parts. In the case of stations 1 and 2, the empty containers 3 to be filled are placed in unordered fashion, and are oriented. The containers 3 are subsequently fed in ordered fashion to a capsule holder 42 of a conveyor wheel 40. The containers 3, closed till now, are opened in station 3. The container 3 is filled with the product 2 in station 5. The filled container 3 is closed in station 7. The containers 3 are weighed in station 8 by a weighing device 44. The weighing device 44 can undertake different measurements. Firstly, the weighing device 44 can undertake to weigh the empty or filled container 3 for initialization. The weighing device 44 could also be used for comparative weighing while production is proceeding in order to check the measurement system described, which is based on x-radiation. The closing pressure for the closed container 3 is monitored in station 9. Depending on the test in station 9, defective containers 3 in station 10 are ejected for the first time in ordered fashion in station 11. In station 11, the containers 3 pass upward from the capsule holder 42 into the radiation path 36 of an x-ray source 28. Depending on the weight of the product 2 as determined in step 103, defective containers 3 can still be discarded with the aid of a switch 46.

Figure 6:
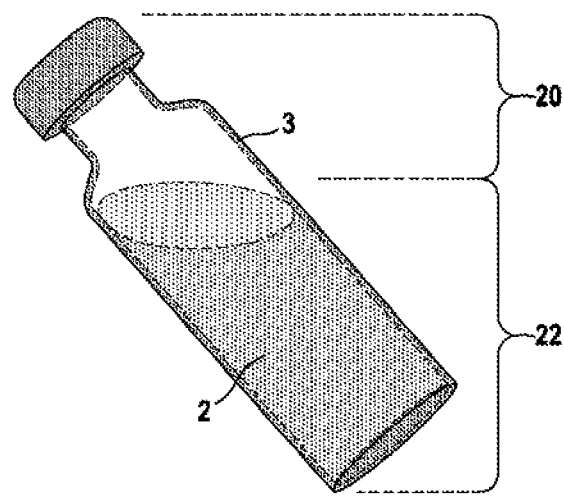
FIG. 6 shows another filled container.

In the exemplary embodiment in accordance with FIG. 6, an ampoule which is filled with a liquid product 2 is provided as container 3. For this product, as well, it is possible to define a region 22 which cannot be freely x-rayed, and a region 20 which can be freely x-rayed.

FIG. 7 illustrates a once again modified device 10 for determining weight. The device 10 has a conveyor wheel 51 which is turned in stepwise fashion in a vertically arranged axis of rotation 52. Accommodating means 54 for the exchangeable fastening of format parts 55 are formed on an annular, vertically oriented outer wall 53 of the conveyor wheel 51 at regular angular spacings. Respectively formed in the format parts 55 are a plurality of accommodating bores 56 which, in particular, are likewise vertically oriented, act as accommodating means for the containers 3 and each have a height and/or length which enables a plurality of containers 3 to be respectively accommodated one above another in a row in the accommodating bores 56. Moreover, the format parts 55 respectively have at least one reference object 35 which is arranged next to the accommodating bores 56 likewise in the radiation path 36 of the x-ray source 28. The format parts 55 consist of a material, in particular of plastic, which is transparent to the x-radiation. The accommodating bores 56 of the format parts 55 are filled with the containers 3 by means of shaft-like feeding channels 57 from a bulk store (not shown), blocking devices respectively being arranged in the region of the feeding channels 57 corresponding to the device 10. In the illustrated exemplary embodiment, a plurality of x-ray sources 28 are arranged on the conveyor path of the conveyor wheel 51 outside the outer circumference thereof. In this case, the number of the x-ray sources 28 preferably corresponds to the number of the feeding channels 57 so that, for example when three feeding channels 57 are present, the conveyor wheel 51 is respectively rotated further in stepwise fashion through a range of angular rotation which corresponds to the division of three feeding channels 57. In order that individual containers 3 which have been recognized as "bad" can be discarded from the conveyor wheel 51 and/or the accommodating bores 56 of the format parts 55, there are provided on the further conveyor path of the conveyor wheel 51 downstream of the x-ray sources 28 discarding rams 65 which can be moved up and down in accordance with the double arrow 61 and can enter the accommodating bores 56, designed as stepped bores, of the format parts 55 in order thereby to discard the containers 3 located in the region of the accommodating bore 56. The device 10 also comprises a weighing device 44 for training purposes, as described below.

Figure 7:
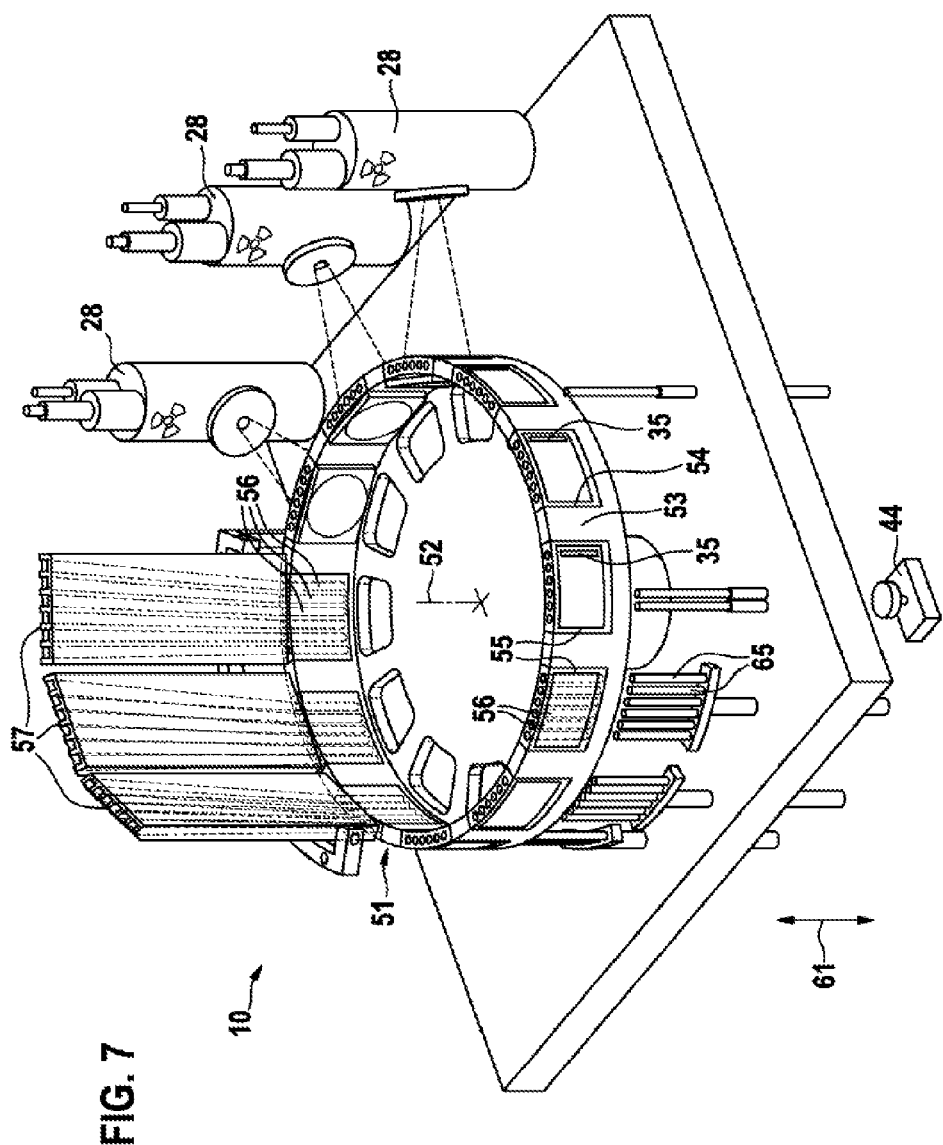
FIG. 7 shows a once again modified device for determining weight.
Figure 8:
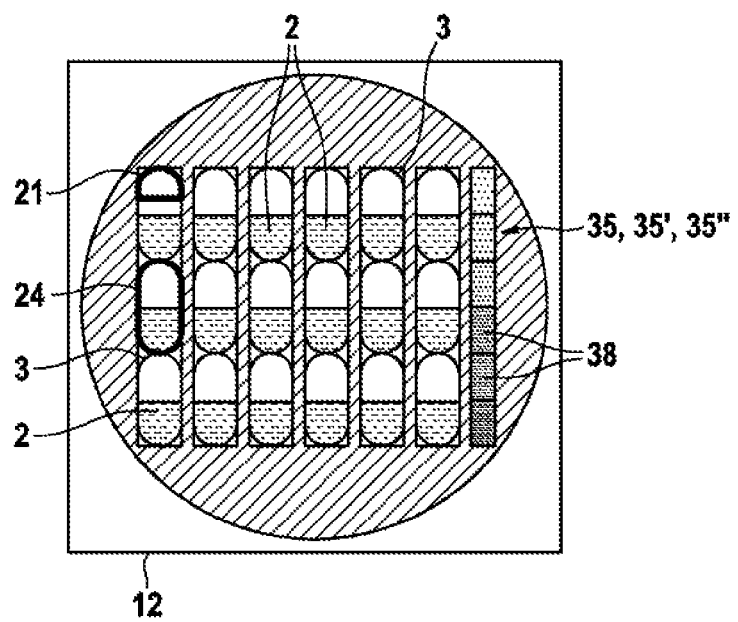
FIG. 8 shows an image of a plurality of irradiated containers and of the reference object for an arrangement according to FIG. 7.

The image 12 in accordance with FIG. 8, which is produced in the arrangement according to FIG. 7, firstly shows the x-ray image of a plurality of containers 3 arranged next to and above one another. Visible on the right-hand side is the image of the irradiated reference object 35 which has different gray tones 38. The reference object 35 is constructed in the form of scale steps with different thicknesses. In the case of the respective different thicknesses, different gray tones 38 are produced, as is stated in more detail below. For example, the evaluation region 21 and the contour 24 of the container 3 are already established and/or determined.

In an alternative embodiment, at least a second reference object 35' is provided which is arranged in the radiation path 36 of the x-ray source 28 and has different thicknesses. In this case, one of the reference objects 35', 35" could be adapted to the material of an empty container 3, and the other could be adapted to the container filling 2. The more that the empty container 3 and product 2 differ from one another with reference to their absorption properties, the greater the increases in accuracy which can be attained thereby. In the tare adjustment, the reference object 35' tuned to the empty container 3 would be used to construct the reference line. In the gross adjustment, the further reference object 35" tuned to the container filling would be used to construct the reference line. In the subsequent actual measurement, the empty container extrapolation is carried out again with the aid of the reference object 35' tuned to the empty container, while the gross measurement is carried out with the aid of the further reference object 35" tuned to the container filling. The conversion into virtual volume and thus into the weight is thus carried out in a differentiated manner, depending on the material being considered, and leads to a once more improved accuracy.

The image 12 is evaluated firstly with regard to the contour 24 of the container 3. To this end, the gray scale values assigned to the respective pixels are evaluated. Said gray scale values are compared with such gray scale values as are produced upon irradiation of the known reference object 35.

In principle, weight is determined in accordance with the arrangement shown in FIG. 1, as described in general below. The reference object 35 advantageously consists of a material which has atomic properties similar to the pharmaceutical product 2 to be irradiated, that is to say, in particular, has the same attenuation properties for the x-radiation. The reference object 35 has different thicknesses considered over the cross section. The reference object 35 can be of wedge-shaped design. Alternatively, the reference object 35 has a row of steps which effect a discrete change in the thickness of the reference object 35. It is preferred to provide that the attenuation (gray scale value) of the reference object 35 is greater at one site and less at another site than the attenuation owing to the pharmaceutical product 2. Owing to the geometrical form of the reference object 35 that has been mentioned, these have different thicknesses which produce different gray tones 38 at the sensor element 30 upon irradiation by means of the x-ray source 28. Individual steps of the reference object 35 have different gray scale values 38.

The weight of the product 2 located in a container 3 is determined as follows, in principle: in an adjusting process (not shown) that takes place in advance, an image of the reference object 35 is recorded, and its gray scale values 38 detected by the sensor device 30 are assigned to the thicknesses of the reference object 35 on the basis of the known geometrical design of the reference object 35. In other words, what this means is that a specific thickness of the reference object 35 at a specific site is inferred on the basis of a specific gray scale value 38 of the reference object 35. Furthermore, a specific thickness can therefore be assigned to a specific gray scale value 38 of the reference object 35 on the basis of the known geometry of the reference object 35. Said gray scale values 38 determined in advance in the calibration process, and their geometric assignment to the reference object 35, are stored in the evaluation device 14. If the aim is now, for example, to detect and/or check the weight, the image 12, acquired by the sensor element 30, of the container 3 is split into individual pixels. Said pixel displays a specific area, for example a square with an edge length of 100 ☐m. The detected gray scale value of the pixel is then assigned to an (identical) gray scale value 38 on the reference object 35 for each pixel of the container 3. A specific thickness can be assigned to said gray scale value (on the basis of the assignment of the thicknesses to the gray scale values 38 on the reference object 35). Once this has been done pixel by pixel, a mean thickness is determined from individual thicknesses. Said mean thickness is now multiplied by the total number of the pixels and their known area so that a virtual volume of the product 2 can be determined. Finally, the weight of the product 2 located in the container 3 can be determined from the virtual volume.

An image of the relevant reference object 35 is also concomitantly recorded simultaneously during the x-ray of the products 2, in particular pharmaceutical ones. Changes in the gray tones on the reference object 35 can thereby be determined on temporally consecutive images which can occur owing to interference of the system or external interference. By way of example, should it be established that the gray scale value 38 of the reference object 35 changes at a specific step, the evaluation device 14 can verify said detected current gray scale value with a correction factor or offset, the result being that the current gray scale value is adapted to the original gray scale value, and the interference is thereby equalized. On the basis of said general procedure, the net weight is determined in accordance with the invention as described below by means of empty container extrapolation.

The device 10 according to the invention operates as follows. In a first step 101, the system is trained to the empty containers 3 being used. To this end, it is at least one empty container 3 and the reference element 35 arranged next to it that are irradiated. The sensor 30 situated downstream acquires the radiation falling onto the sensor surface 32 in the form of an image 12 with different gray scale values. Said image 12 is firstly evaluated to detect the contour, for example in that the contour 24 of the container 3 is inferred pixel by pixel in the case of a specific transition of gray scale values and/or threshold value.

Subsequently, only such pixels as lie within the determined contour 24 of the container 3 are evaluated. The gray scale value of the respective pixel which lies within the contour is used to construct a reference line. The respective gray scale value is compared with that gray scale value 38 of the reference object 35 whose related thickness is known. A thickness is thus assigned to the respective pixel. This is performed for all pixels lying within the contour 24, the result being a mean thickness for the known area of the contour 24. A weight can be assigned to said volume. To this end, a weighing device 44 acquires the weight of the empty container 3. This is called tare adjustment. The attenuation curve makes the connection between the respective gray scale values of the image 12 and/or pixel and the related empty weight of the container 3.

In a second step 102, the system is trained to the containers 3 trained in the first step 101, but now filled with product 2. Once again, a reference line of the container 3 with product 2 is constructed as already done above (described for an empty container 3), the relation to the gravimetric weight being produced using the weighing device 44 which determines the weight of a container 3 filled with product 2. The so-called gross adjustment is performed in this way. Once again, the respective gray scale values are assigned via the determined reference line to the corresponding weight of a filled container 3. Said training steps 101 and 102 are executed before the start of the production phase of a new charge which differs from the preceding one both in the type of container 3 and/or of the filled product 2. Said steps 101 and 102 can be carried out with a plurality of different containers 3, and the results can be suitably averaged and/or interpolated.

Alternatively, it could be provided that the operating parameters of a device 10 (as described above, for example) which is set uniquely for specific charge parameters can be stored and reloaded later for a similar charge. The adjustment steps 101 and 102 described could then be superfluous.

In a third step 103, the sensor 30 produces an image 12 of the container 3 which is located in the radiation path 36, is to be checked and is filled with product 2. The weight of the product 2 is to be determined by means of empty container extrapolation.

In a fourth step 104, at least one evaluation region 21 is established in the image 12 acquired in step 103. To this end, the contour 24 of the irradiated container 3 can firstly be determined via appropriate image recognition. With the aid of the determined gray tones, the position or the geometry of the container 3 and/or with knowledge of the filled product 2, the evaluation region 21 is then selected so that there is certainly no product 2 located in said evaluation region 21. By way of example, at least the evaluation region 21 could be established manually in the course of the training phase by the operating staff via appropriate inputs. Alternatively, said establishing process could also be performed automatically on the basis of gray scale value, contour 24 of the container 3 or information relating to the volume to be expected of the filled product 2. The selected evaluation region 21 is established once and retained for the subsequent steps for detecting weight. The subsequent steps 105 to 107 are then carried out as the production operation proceeds.

In a fifth step 105, the evaluation region 21 established in step 104, specifically the part of the container 3 which can be freely x-rayed, is evaluated. The pixels lying in the evaluation region 21 are evaluated as described above with reference to their gray scale values. On the basis of said information and the reference line for an empty container 3 determined in the first step 101, the empty weight of the container 3 x-rayed in the third step 103 is now extrapolated. The tare weight of the container 3 is thus determined. By way of example, in this case the ratio is formed between the area of the evaluation region 21 and the total area of the container 3, in order thus to infer the total weight of the empty container 3. The total area of the container 3 can be determined via the detected contour 24. The number of the pixels lying within the contour 24, whose magnitude is known, is a measure of the total area. However, other options would also be conceivable for the determination. By means of the weight of the portion of the area of the evaluation region 21 with reference to the total area of the container 3, extrapolation to the weight of the complete empty container 3, the tare weight which is available at the end of step 105, is performed.

In a sixth step 106, the whole container 3 including product 2 is evaluated on the basis of the image 12 acquired in the third step 103. For this purpose, all pixels lying within the contour of the entire container 3 are evaluated together with their gray scale values. The gross weight of the container 3 irradiated in the third step 103 is now determined from said information and the reference line for a filled container 3 determined in the second step 102. A procedure for the corresponding determination of gross weight is as described above in general. The gray scale values of container 3 and product 2 overlap one another. Consequently, the determination of weight based on the gray scale values comprises both the weight of the empty container 3 and the weight of the product 2.

In a seventh step 107, the net weight of the product 2 is determined in accordance with the relationship: net weight=gross weight (as determined in the sixth step 106)−tare weight (as determined in the fifth step 105). The result is thus the pure net weight of the container filling, that is to say the weight of the product 2.

Owing to the procedure described, the net weight of the product 2 is determined in targeted fashion, and no longer only the gross weight of container 3 and product 2, as in the prior art. This is particularly important especially in the case of small filling quantities, since in said instances the weight of the container 3 greatly influences the accuracy of the determination of weight. Thus, given small filling quantities, manufacturing fluctuations in the tare weight of empty containers 3 can be greater than maximum permissible fluctuations in filling quantities. This can result in containers 3 with the correct filling quantity of the product 2 being rejected as incorrectly filled, because the tare weight of the container 3 has exhausted the weight tolerance. Conversely, this can also have the effect that a container 3 filled with too much or too little filled product 2 is wrongly recognized as being in order, because the tolerated container weight fluctuation has the opposite effect and compensates the erroneous dosing. The net weight determination described counteracts said unacceptable cases by means of empty container extrapolation.

The procedure described is suitable, in particular, for pharmaceutical hard gelatin capsules, but also for tablets, glass containers such as vials, ampoules or the like, but is not restricted thereto.

What is claimed is:

1. A device for determining weight of a container (3) filled with product (2), comprising
    at least one x-ray source (28) which produces a radiation path (18) for irradiating the container (3),
    at least one sensor (30) which detects radiation of the irradiated container (3) in the form of an image (12), wherein the image (12) of the irradiated container (3) is subdivided into at least one evaluation region (21) in which no product (2) is located, and
    an evaluation device (14) which determines a tare weight of the irradiated container (3) by using a ratio formed between a measure of an area of the evaluation region (21) and a measure of an area of a contour (24) of the entire irradiated container (3).

2. The device as claimed in claim 1, characterized in that the evaluation device (14) uses the image (12) to determine a gross weight of the irradiated container (3), and subsequently uses the gross weight and the tare weight to determine a net weight of the product (2) located in the container (3).

3. The device as claimed in claim 1, characterized in that the evaluation device (14) evaluates at least one of gray scale values and pixels of the sensor (30) lying within at least one of the evaluation region (21) and the contour in order to determine the tare weight.

4. The device as claimed in claim 3, characterized in that as a measure of an area of at least one of the evaluation region (21) and of the contour (24), the evaluation device (14) uses such pixels of the sensor (30) as lie within at least one of the evaluation region (21) and within the contour (24).

5. The device as claimed in claim 1, characterized in that for training purposes the x-ray source (28) irradiates at least one of an empty container (3) and a container (3) filled with product (2), and in that for training purposes the evaluation device (14) constructs a reference line which assigns an appropriate weight to different gray scale values.

6. The device as claimed in claim 5, further comprising a weighing device (44) which detects the weight of the container (3) and the evaluation device (14) determines the reference line by taking account of the detected weight.

7. The device as claimed in claim 1, further comprising at least one reference object (35) which is arranged in the radiation path (18) of the x-ray source (28) and which has different thicknesses.

8. The device as claimed in claim 1, further comprising an accommodating means for accommodating at least one container (3), wherein the container (3) is fed via a conveying means (40) to at least one of a processing station (43) and the x-ray source (28) in order to produce the image (12).

9. A method for determining the weight of a container (3) filled with product (12), the method comprising
    producing, via at least one x-ray source (28), a radiation path (18) for irradiating the container (3),
    detecting, with at least one sensor (30), radiation of the irradiated container (3) in the form of an image (12),
    subdividing the image (12) of the irradiated container (3) into at least one evaluation region (21) in which no product 2 is located, and
    determining a tare weight of the irradiated container (3) by using a ratio formed between a measure of an area of the evaluation region (21) and a measure of an area of a contour (24) of the entire irradiated container (3).

10. The method as claimed in claim 9, characterized in that the image (12) is used to determine a gross weight of the irradiated container (3), and subsequently the gross weight and the tare weight are used to determine a net weight of the product (2) located in the container (3).

11. The method as claimed in claim 9, characterized in that at least one of gray scale values and pixels of the sensor (30) lying within at least one of the evaluation region (21) and the contour (2324) are evaluated in order to determine at least one of the weight and a measure of at least one of an area of the evaluation region (21) and the contour (24).

12. The method as claimed in claim 9, characterized in that for training purposes at least one of an empty container (3) and a container (3) filled with product (2) is irradiated, and in that for training purposes a reference line is constructed which assigns an appropriate weight to different gray scale values.

13. The method as claimed in claim 9, characterized in that at least one reference object (35) is irradiated and gray scale values (38) occurring thereby are assigned to corresponding thicknesses of the reference object (35), for the purpose of determining at least one of tare weight and gross weight the gray scale values of the sensor (30) being assigned to the thickness of the reference object (35) which corresponds to the respective gray scale value (38) of the reference object (35).

* * * * *